US012727759B2

(12) United States Patent
Okamoto et al.

(10) Patent No.: US 12,727,759 B2
(45) Date of Patent: Sep. 8, 2026

(54) OPHTHALMIC DEVICE

(71) Applicant: Tomey Corporation, Nagoya (JP)

(72) Inventors: Keiichiro Okamoto, Nagoya (JP); Guangchun Bian, Nagoya (JP)

(73) Assignee: TOMEY CORPORATION, Nagoya (JP)

( * ) Notice: Subject to any disclaimer, the term of this patent is extended or adjusted under 35 U.S.C. 154(b) by 859 days.

(21) Appl. No.: 18/117,066

(22) Filed: Mar. 3, 2023

(65) Prior Publication Data

US 2023/0284901 A1 Sep. 14, 2023

(30) Foreign Application Priority Data

Mar. 8, 2022 (JP) ................................ 2022-035625

(51) Int. Cl.

| | |
|---|---|
| ***A61B 3/14*** | (2006.01) |
| ***A61B 3/00*** | (2006.01) |
| ***A61B 3/10*** | (2006.01) |
| ***A61B 3/103*** | (2006.01) |
| ***A61B 3/12*** | (2006.01) |

(52) U.S. Cl.

CPC ............. *A61B 3/14* (2013.01); *A61B 3/0025* (2013.01); *A61B 3/1015* (2013.01); *A61B 3/103* (2013.01); *A61B 3/12* (2013.01)

(58) Field of Classification Search

CPC ..... A61B 3/0025; A61B 3/1015; A61B 3/103; A61B 3/12; A61B 3/14

See application file for complete search history.

(56) References Cited

U.S. PATENT DOCUMENTS

| | | | |
|---|---|---|---|
| 2005/0157261 | A1 | 7/2005 | Hanebuchi et al. |
| 2020/0100674 | A1 | 4/2020 | Yamanari et al. |
| 2023/0079050 | A1 | 3/2023 | Okamoto |

FOREIGN PATENT DOCUMENTS

| | | | |
|---|---|---|---|
| EP | 4147628 | A1 | 3/2023 |
| JP | 2005-185523 | A | 7/2005 |
| JP | 2019-058470 | A | 4/2019 |
| JP | 2020-202904 | A | 12/2020 |

*Primary Examiner* — Jack Dinh

(74) *Attorney, Agent, or Firm* — Jason A. Smith; Shumaker, Loop & Kendrick, LLP

(57) ABSTRACT

An ophthalmic device may include: a measurement optical system which includes a light-emitting optical system including a light source and a light-receiving optical system including a light receiving element; an arithmetic device configured to calculate an eye refractive power of the subject eye; a beam deflecting member arranged in an optical path of the measurement optical system and configured to deflect beam emitted from the light source, and a driving device configured to drive the beam deflecting member so that the beam emitted from the light source is scanned in a ring shape onto the subject eye. The beam deflecting member may be disposed so that traveling directions of the beam emitted from the light source intersect with each other between the subject eye and the beam deflecting member when the beam deflecting member is driven by the driving device.

6 Claims, 16 Drawing Sheets

10
20
E
L1
L2
L3
L4
108
110
120
122
124
126
128
130
132
134
136
138
140
142
144
146
148
150
152
154
156
158
160
162
164
166
168
170
172

20
142
140
138
136
120
134
L2
L3
130
122
152
132
124
150
154
156
158
148
172
126
108
110
128
168
170
L4
166
162
L1
144
164
160
146
E 20
142
140
138
136
120
134
L2
L3
130
122
152
132
124
150
158
154
156
L4
170
168
148
172
126
108
110
128
166
162
L1
144
164
160
146
E 20
142
140
136
120
138
134
L2
L3
152
130
122
150
154
156
158
124
132
148
126
172
170
L4
168
108
110
128
166
162
L1
144
164
160
146
E

OPHTHALMIC DEVICE

CROSS-REFERENCE TO RELATED APPLICATION

This application claims priority to Japanese Patent Application No. 2022-035625, filed on Mar. 18, 2022, the entire contents of which are incorporated herein by reference.

TECHNICAL FIELD

The art disclosed herein relates to an ophthalmic device.

BACKGROUND

Japanese Patent Application Publication No. 2005-185523 (JP 2005-185523 A) describes an ophthalmic device configured to measure eye refractive power. This device includes a measurement optical system including a light-emitting optical system and a light-receiving optical system, an arithmetic unit, a beam deflecting member, and a rotary unit. The light-emitting optical system is configured to emit a spotlight beam (beam in a spot shape) to a fundus of a subject eye. The light-receiving optical system is configured to extract reflected light from the fundus of the subject eye and receives the same with a light receiving element. The arithmetic unit is configured to measure the eye refractive power based on an output from the light receiving element. The beam deflecting member is arranged on an optical path of the measurement optical system at a position displaced from a position conjugate with a pupil. The rotary unit is configured to rotate the beam deflecting member about an optical axis.

SUMMARY

In JP 2005-185523 A, the beam emitted as a spotlight beam is deflected by the beam deflecting member that rotates about the optical axis, and the beam is thereby scanned in a ring shape on the fundus. The beam deflected by the beam deflecting member may travel inside the subject eye while being tilted relative to an optical axis of the ophthalmic device. Due to this, a scanning diameter of the beam emitted on the fundus may change according to an eye axis length of the subject eye. As a result, depending on the eye axis length of the subject eye, the beam emitted to the fundus may be scanned at a position distant from a fovea, and the measured value thereof may deviate from an examined value of subjective refractive power. The description herein proposes an art that enables to suitably emit beam onto a fundus of a subject eye regardless of an eye axis length of the subject eye.

An ophthalmic device disclosed herein may comprise: a measurement optical system which includes a light-emitting optical system including a light source configured to emit light beam in a spot shape onto a fundus of a subject eye and a light-receiving optical system including a light receiving element configured to receive reflected light from the fundus of the subject eye; an arithmetic device configured to calculate an eye refractive power of the subject eye based on an output of the light receiving element; a beam deflecting member arranged in an optical path of the measurement optical system and configured to deflect the beam emitted from the light source; and a driving device configured to drive the beam deflecting member so that the beam emitted from the light source is scanned in a ring shape onto the subject eye. The beam deflecting member may be disposed so that traveling directions of the beam emitted from the light source intersect with each other between the subject eye and the beam deflecting member when the beam deflecting member is driven by the driving device.

In the above ophthalmic device, the beam is scanned in the ring shape on the subject eye when the beam deflecting member is driven by the driving device, and the traveling directions of the beam intersect each other between the subject eye and the beam deflecting member. That is, in this ophthalmic device, the beam deflected by the beam deflecting member enters the subject eye by being tilted in directions separating away from the optical axis of the ophthalmic device. Due to this, when the beam scanned in the ring shape passes through a subject eye lens (that is, a lens contemplated by regarding the subject eye as one lens), the beam travels with its traveling directions refracted in directions which are closer to being parallel (to each other). As such, in this ophthalmic device, the scanning diameter of the beam emitted onto the fundus does not change so much in either case where the eye axis length of the subject eye is relatively long or relatively short, and the beam can suitably be scanned in the ring shape on the fundus of the subject eye.

DETAILED DESCRIPTION

Figure 1:
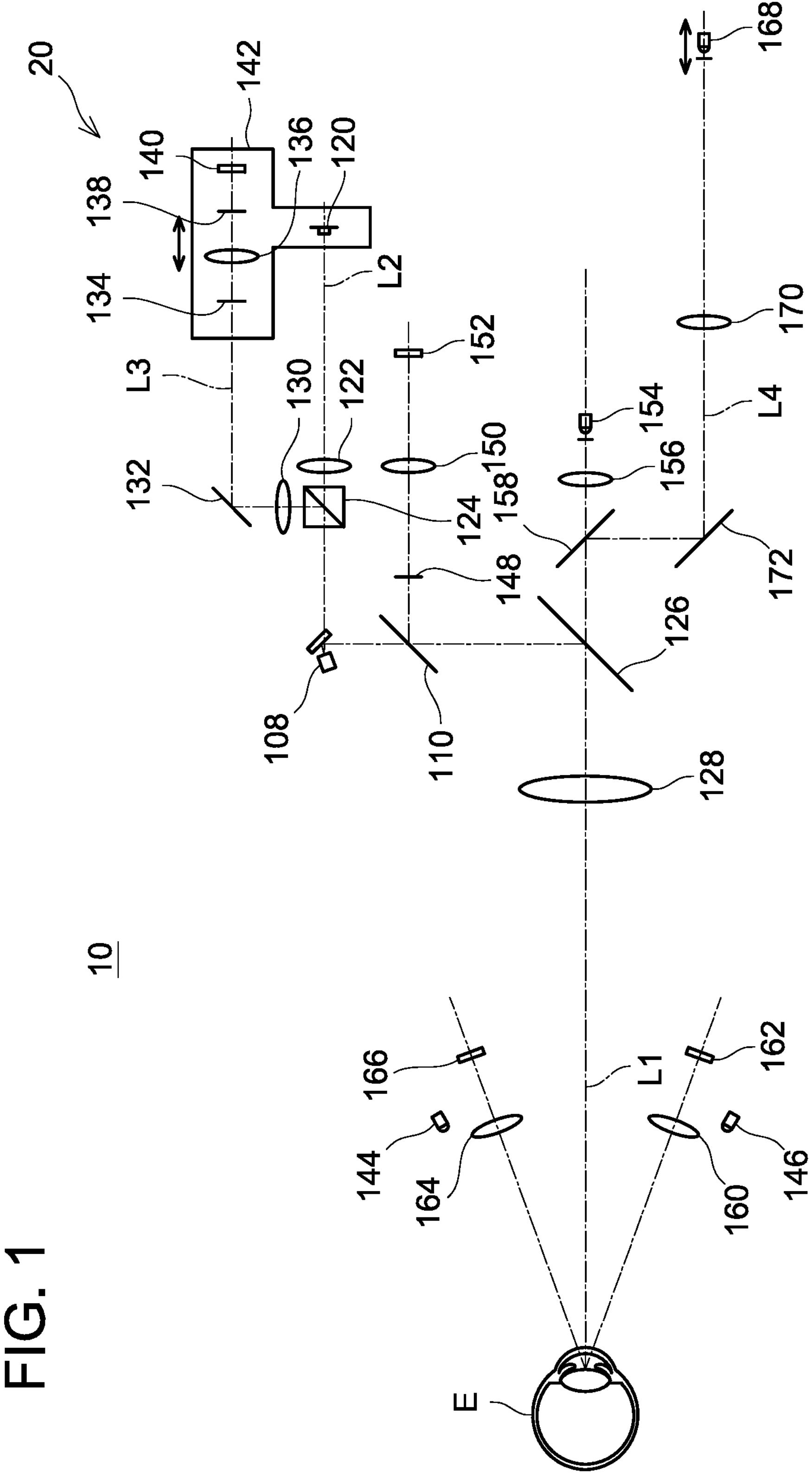
FIG. 1 is a schematic configurational diagram of optical systems of an ophthalmic device of a first embodiment.

Representative, non-limiting examples of the present disclosure will now be described in further detail with reference to the attached drawings. This detailed description is merely intended to teach a person of skill in the art further details for practicing preferred aspects of the present teachings and is not intended to limit the scope of the present disclosure. Furthermore, each of the additional features and teachings disclosed below may be utilized separately or in conjunction with other features and teachings to provide improved ophthalmic devices, as well as methods for using and manufacturing the same.

Moreover, combinations of features and steps disclosed in the following detailed description may not be necessary to practice the present disclosure in the broadest sense, and are instead taught merely to particularly describe representative examples of the present disclosure. Furthermore, various features of the above-described and below-described representative examples, as well as the various independent and dependent claims, may be combined in ways that are not specifically and explicitly enumerated in order to provide additional useful embodiments of the present teachings.

All features disclosed in the description and/or the claims are intended to be disclosed separately and independently from each other for the purpose of original written disclosure, as well as for the purpose of restricting the claimed subject matter, independent of the compositions of the features in the embodiments and/or the claims. In addition, all value ranges or indications of groups of entities are intended to disclose every possible intermediate value or intermediate entity for the purpose of original written disclosure, as well as for the purpose of restricting the claimed subject matter.

Hereinbelow, some of technical elements disclosed herein are listed. The respective technical elements as below are each independently useful.

In an embodiment of the present technology, the beam deflecting member may be arranged at a position conjugate with an intersecting position where the traveling directions of the beam intersect with each other.

According to such a configuration, the traveling directions of the beam (i.e., rays) can easily be caused to intersect each other between the subject eye and the beam deflecting member.

In an embodiment of the present technology, the light-receiving optical system may further include an optical member arranged at a position conjugate with the fundus of the subject eye and configured to condense the reflected light in a ring shape on the light receiving element.

According to such a configuration, a ring image formed on the light receiving element can be analyzed by elliptic approximation, and spherical power and cylindrical power of the subject eye can thereby be calculated.

In an embodiment of the present technology, the light receiving optical system may further include an optical member having a plurality of lenses arranged in a grid pattern at a position conjugate with the fundus of the subject eye, the lenses being configured to condense the reflected light in a shape of dots constituting a grid pattern on the light-receiving element.

According to such a configuration, a distortion in a wavefront generated by an eyeball of the subject eye (that is, total aberration of the eyeball) can be measured based on a position coordinate of the reflected light inputted to the light receiving element in a dot grid pattern.

In an embodiment of the present technology, the driving device may be configured to drive the beam deflecting member so that the traveling directions of the beam entering the subject eye are substantially parallel inside the subject eye.

According to such a configuration, the beam can be emitted with high precision onto the fundus of the subject eye regardless of the eye axis length of the subject eye.

In an embodiment of the present technology, if a>f, a position of the beam deflecting member or a swing angle of the beam may be set so as to satisfy the following formula (1);

$$1.5 \geq 2(a' + 1.4)\left\{1 - 13.6\left(\frac{1}{17.1} - \frac{1}{a' + 1.4}\right)\right\}\tan\theta \tag{1}$$

if a<f, the position of the beam deflecting member or the swing angle of the beam may be set so as to satisfy the following formula (2);

$$1.5 \geq 2(a' + 1.4)\left\{1 - 22.9\left(\frac{1}{17.1} - \frac{1}{a' + 1.4}\right)\right\}\tan\theta \tag{2}$$

Where a is a distance from a principal point of a subject eye lens to an intersecting position where the traveling directions of the beam intersect with each other, f is a focal length of the subject eye lens and is 17.1 mm, a diameter of a fovea of the subject eye is 1.5 mm, a' is a distance from a corneal apex of the subject eye to the intersecting position, and θ is an angle formed by the beam entering the subject eye lens from the intersecting position and an optical axis of the ophthalmic device.

According to such a configuration, the beam can be scanned in the ring shape with a scan diameter smaller than a diameter of the fovea of the subject eye regardless of the eye axis length of the subject eye of a subject.

First Embodiment

Hereinbelow, an ophthalmic device 10 of a first embodiment will be described. The ophthalmic device 10 of the present embodiment is a device for measuring eye refractive power which is configured to measure objectively eye refractive power of a subject eye E. The ophthalmic device 10 comprises an optical system 20 shown in FIG. 1. The optical system 20 comprises a refractive power measurement optical system, a front monitor optical system, a position detecting light-emitting optical system, a position detecting light-receiving optical system, a gaze fixing optical system, and an observation optical system (not shown)

for observing the subject eye E. Since configurations that are used in well-known ophthalmic devices can be used as the observation optical system, the detailed description thereof will be omitted. Hereinbelow, an ideal optical arrangement that is set for an ideal subject eye E (such as a Gullstrand's schematic eye) will firstly be explained.

Figure 2:
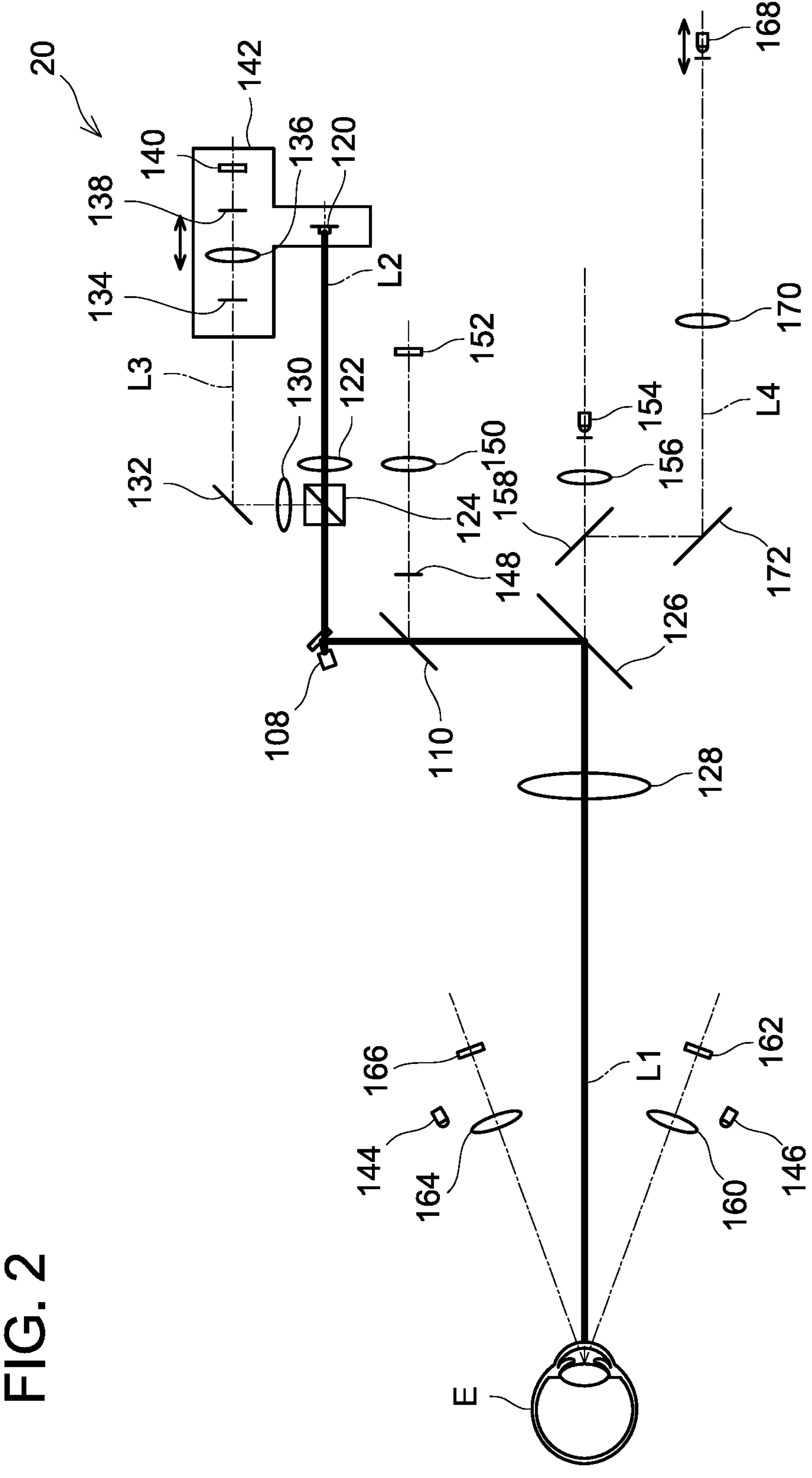
FIG. 2 is a diagram for explaining a light-emitting optical system in a refractive power measurement optical system of the ophthalmic device of the first embodiment.

As shown in FIG. 2, a light-emitting optical system in the refractive power measurement optical system is constituted of a light source 120, a lens 122, a polarization beam splitter 124, a 2D scanner 108 (an example of beam deflecting member), a dichroic mirror 110, a dichroic mirror 126, and an object lens 128.

The light source 120 is an infrared point light source such as an SLD (Super Luminescent Diode), a LD (Laser Diode), and a LED (Light Emitting Diode). The light source 120 is configured to output light with a central wavelength of 0.83 μm. The light outputted from the light source 120 penetrates through the lens 122 and the polarization beam splitter 124, and is inputted to the 2D scanner 108. The 2D scanner 108 is configured to scan the entering beam (rays) in two directions relative to a fundus of the subject eye E, namely in an x direction and a y direction by being driven by a driving device that is not shown. In the present embodiment, a Galvano scanner is used as the 2D scanner 108. The 2D scanner 108 may employ configurations other than the Galvano scanner, and may for example use a MEMS mirror capable of two-axis scan. The light outputted from the 2D scanner 108 penetrates through the dichroic mirror 110, is reflected on the dichroic mirror 126, and enters the object lens 128. The light inputted to the object lens 128 penetrates through the object lens 128 and is irradiated to the fundus of the subject eye E (such as fovea).

Figure 3:
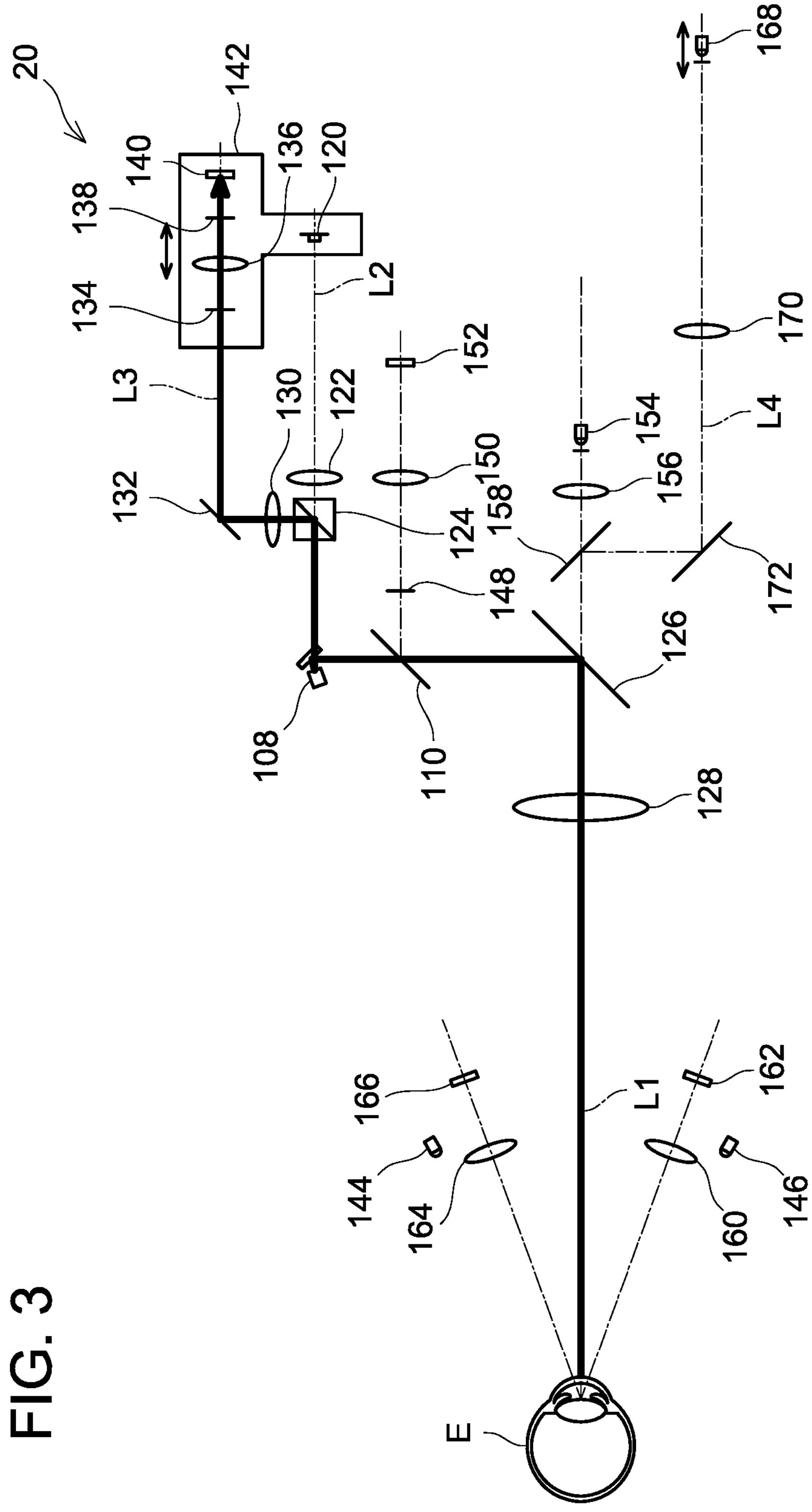
FIG. 3 is a diagram for explaining a light-receiving optical system in the refractive power measurement optical system of the ophthalmic device of the first embodiment.

As shown in FIG. 3, the light-receiving optical system in the refractive power measurement optical system is constituted of the object lens 128, the dichroic mirror 126, the dichroic mirror 110, the 2D scanner 108, the polarization beam splitter 124, a lens 130, a mirror 132, an aperture 134, a lens 136, a ring lens 138 (an example of optical member), a 2D sensor 140 (an example of light receiving element), a focus adjusting mechanism 142, and a fogging mechanism (not shown).

As it is apparent from comparison of FIGS. 2 and 3, a path of light that scattered on the fundus of the subject eye E is on the same path as the light-optical system in a range between the object lens 128 and the polarization beam splitter 124. In the polarization beam splitter 124, only an S polarization component of the light scattered on the fundus of the subject eye E is reflected and is irradiated to the mirror 132 through the lens 130. The light irradiated to the mirror 132 penetrates through the aperture 134, the lens 136, and the ring lens 138.

Figure 4:
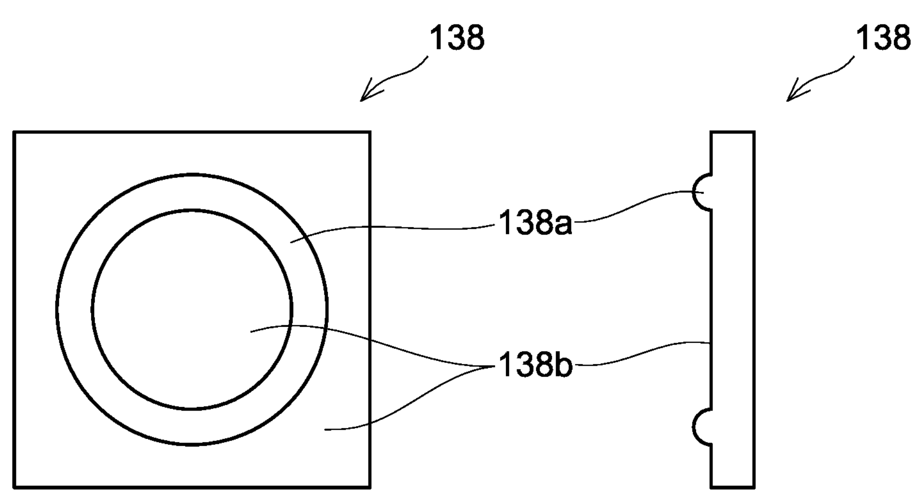
FIG. 4 is a diagram for explaining a configuration of a ring lens.

As shown in FIG. 4, the ring lens 138 is constituted of a lens part **138*a* configured by forming a cylindrical lens in a ring shape on a flat plate, and a light-blocked part 138*b* configured by applying a coating for blocking light in areas other than the lens part 138*a*. The ring lens 138 is arranged such that the light-blocked part 138*b* is located at a position conjugate with the fundus of the subject eye E. Due to this, the reflected light from the fundus can be extracted from an area around a pupil in a ring shape at a size corresponding to the light-blocked part 138*b*. When the reflected light enters the ring lens 138, an image at the same size as the ring lens 138 is formed in a ring shape on a detection surface of the 2D sensor 140. The refractive power of the subject eye E is calculated based on the ring image formed in the 2D sensor 140. For example, refractive power (e.g., spherical power and cylindrical power) of the subject eye E can be calculated by analyzing the ring image formed in the 2D sensor 140** by elliptic approximation.

Figure 5:
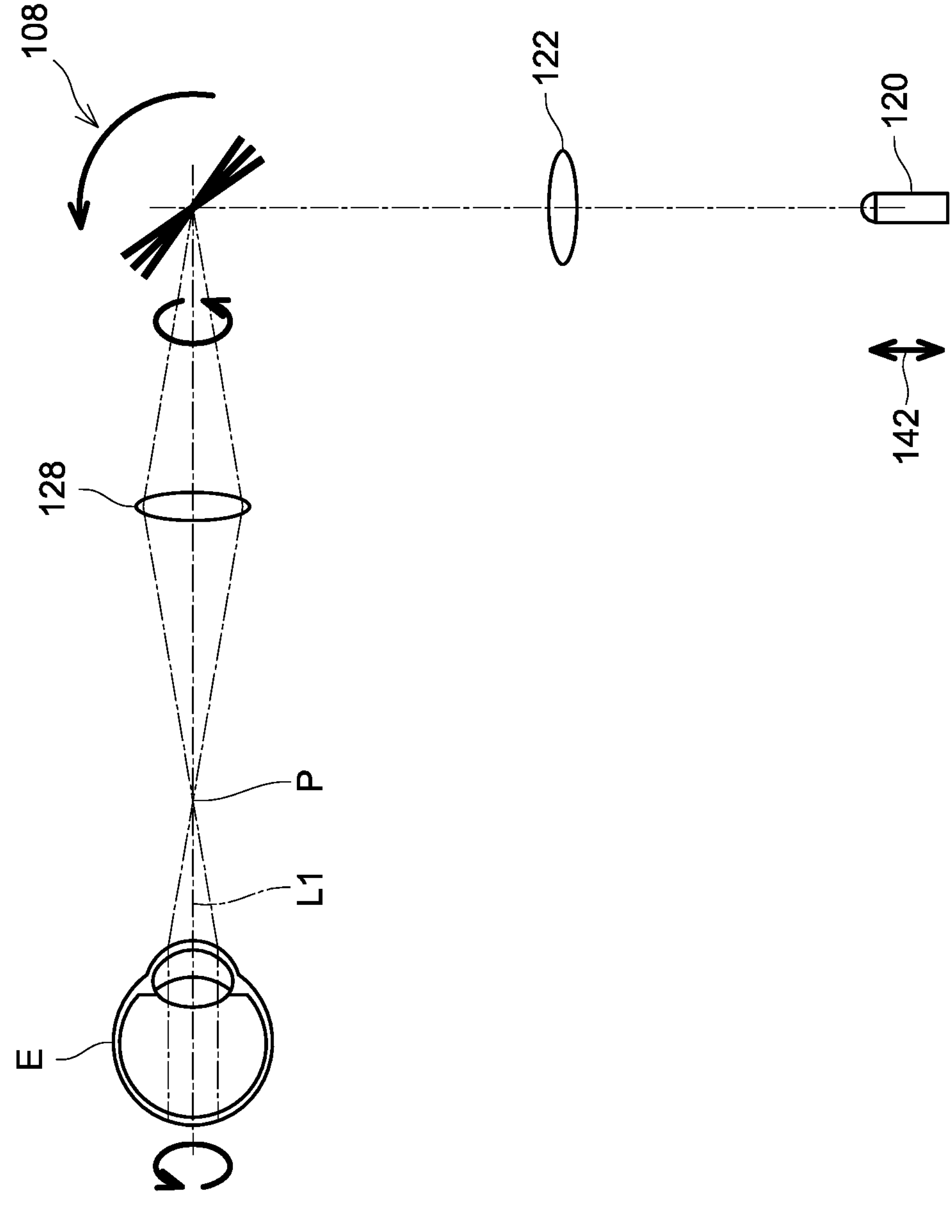
FIG. 5 is a diagram schematically showing an optical path of light in the light-emitting optical system in the refractive power measurement optical system.

Here, scan for measurement beam (i.e., rays) in the refractive power measurement optical system will be described with reference to FIG. 5. FIG. 5 shows an optical path in which the light outputted from the light source 120 is irradiated to the subject eye E. FIG. 5 shows only some of optical members arranged on the optical path (that is, the lens 122, the 2D scanner 108, and the object lens 128) and omits depiction of other optical members. Further, the 2D scanner 108 is arranged at a position conjugate with a range within the optical path L1 between the subject eye E and the object lens 128. Due to this, in the refractive power measurement optical system, the light scanned by the 2D scanner 108 intersects with an optical axis of the ophthalmic device 10 (optical path L1) in the range between the object lens 128 and the subject eye E. That is, in the refractive power measurement optical system, traveling directions of the measurement beam (rays) intersect with each other between the subject eye E and the 2D scanner 108 (more specifically, object lens 128), scan is performed to form a pivot point in front of the subject eye E. Further, in the refractive power measurement optical system, a pivot position (intersecting position) P is set such that the rays of light intersecting with each other between the object lens 128 and the subject eye E become parallel to the optical axis of the ophthalmic device 10 when the rays enter into the subject eye E. That is, in the refractive power measurement optical system, the pivot position P is set to coincide with a front focal point of a lens that is contemplated by regarding the subject eye E as one lens. Due to this, in the refractive power measurement optical system, the light scanned by the 2D scanner 108 reaches the fundus by being substantially parallel to the optical axis of the ophthalmic device 10. That is, telecentric scan is performed in the refractive power measurement optical system, and the measurement beam is scanned in a ring shape while maintaining its position apart from the measuring optical axis at a predetermined distance within the subject eye E and reaches the fundus.

Further, the refractive power measurement optical system includes a focus adjusting mechanism 142. The focus adjusting mechanism 142 includes a moving device (not shown) for integrally moving the light source 120, the aperture 134, the lens 136, the ring lens 138, and the 2D sensor 140 in a direction of the optical axis (optical paths L2, L3). By driving the moving device, the focus adjusting mechanism 142 can move a position of the light source 120 and a position of the 2D sensor 140 to positions that are conjugate with the fundus of the subject eye E according to the refractive power of the subject eye E, and refractive power measurement can be performed with high accuracy.

Figure 6:
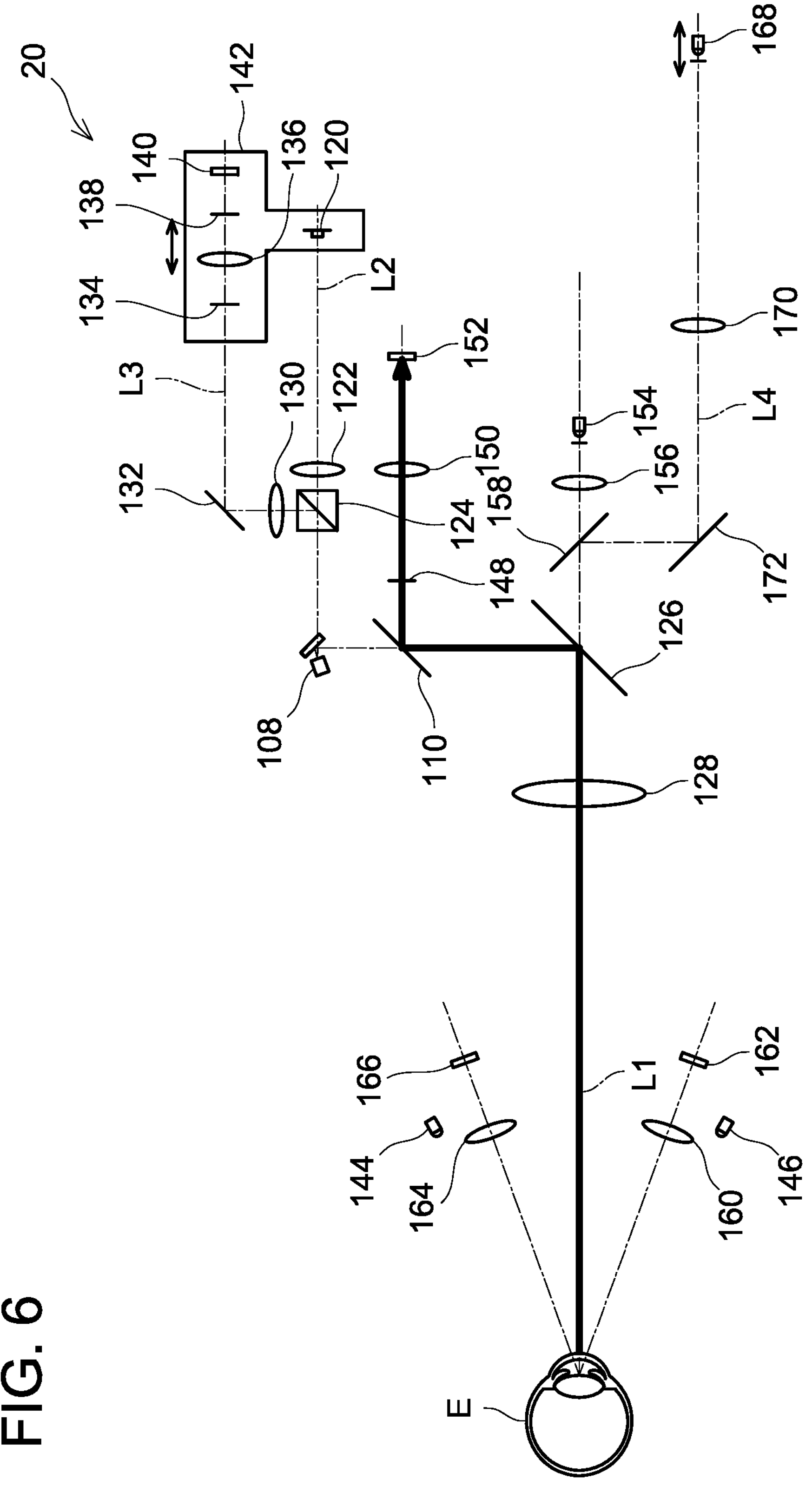
FIG. 6 is a diagram for explaining a front monitor optical system of the ophthalmic device of the first embodiment.

Next, the front monitor optical system will be described. As shown in FIG. 6, the front monitor optical system is constituted of LEDs 144, 146, the object lens 128, the dichroic mirror 126, the dichroic mirror 110, an aperture 148, a lens 150, and a 2D sensor 152.

The LEDs 144, 146 are arranged frontward of the subject eye E at positions diagonally offset toward the sides, and are configured to irradiate light onto an anterior eye part of the subject eye E. The LEDs 144, 146 each output light with a central wavelength of 0.76 μm. The light reflected on the subject eye E penetrates through the object lens 128, is reflected on the dichroic mirrors 126, 110, penetrates through the aperture 148 and the lens 150, and forms a frontal image of the anterior eye part in the 2D sensor 152. The image of the anterior eye part of the subject eye E captured in the 2D sensor 152 is displayed in a display device that is not shown. The aperture 148 is arranged at a rear focal point of the object lens 128 and is configured with an image magnification that remains unchanged even when the anterior eye part image is defocused.

Figure 7:
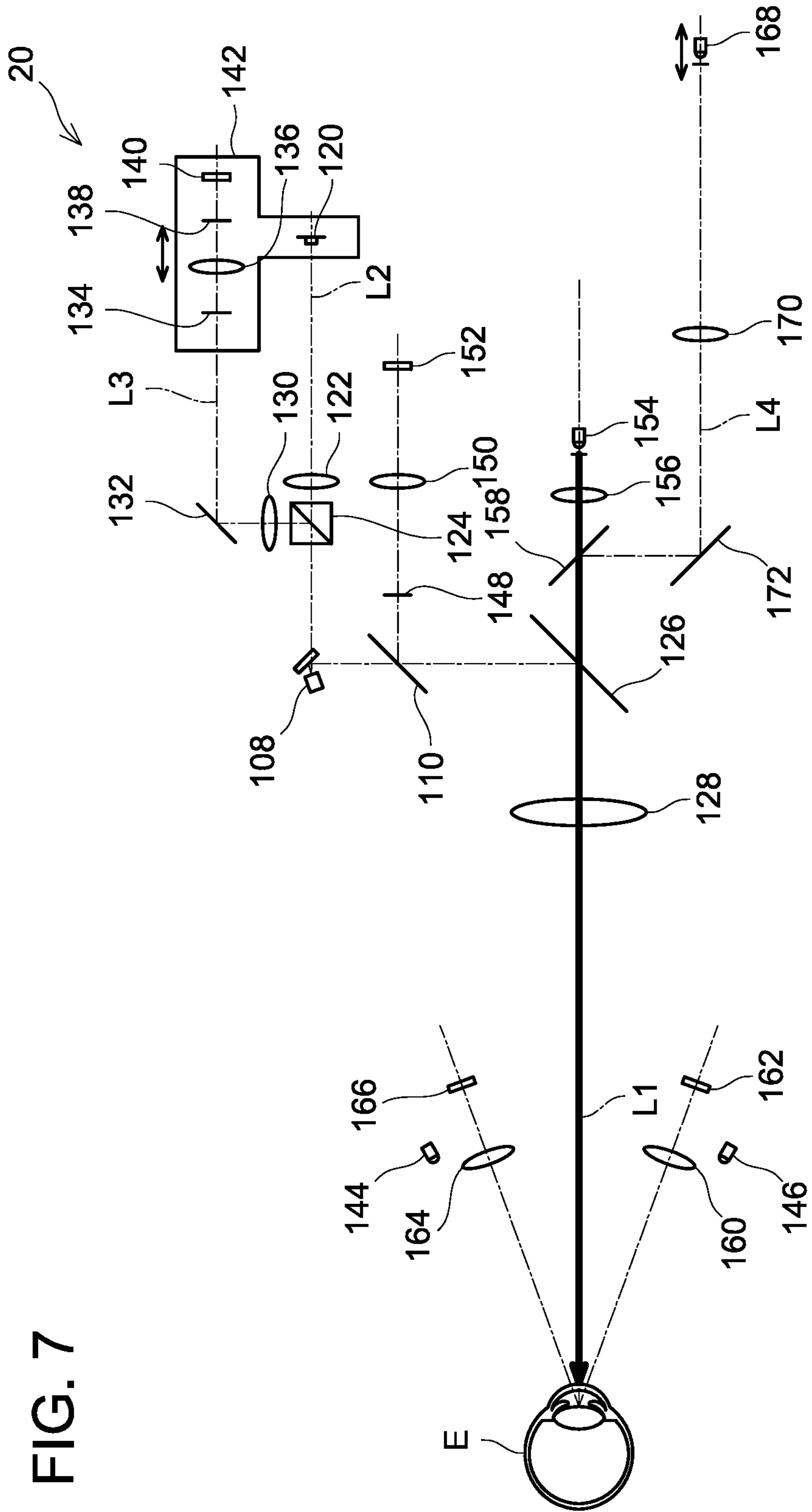
FIG. 7 is a diagram for explaining a position detection light-emitting optical system of the ophthalmic device of the first embodiment.

Next, the position detecting light-emitting optical system will be described. As shown in FIG. 7, the position detecting light-emitting optical system is constituted of a LED 154, a lens 156, a dichroic mirror 158, the dichroic mirror 126, and the object lens 128. The LED 154 outputs light with a central wavelength of 0.94 μm. The light outputted from the LED 154 penetrates through the lens 156, the dichroic mirrors 158, 126, and the object lens 128, and irradiates a cornea of the subject eye E. The light irradiated to the subject eye E is mirror-reflected on a surface of the cornea of the subject eye E, and a virtual image of a light-emitting surface of the LED 154 is formed on an extension line of a corneal apex.

Figure 8:
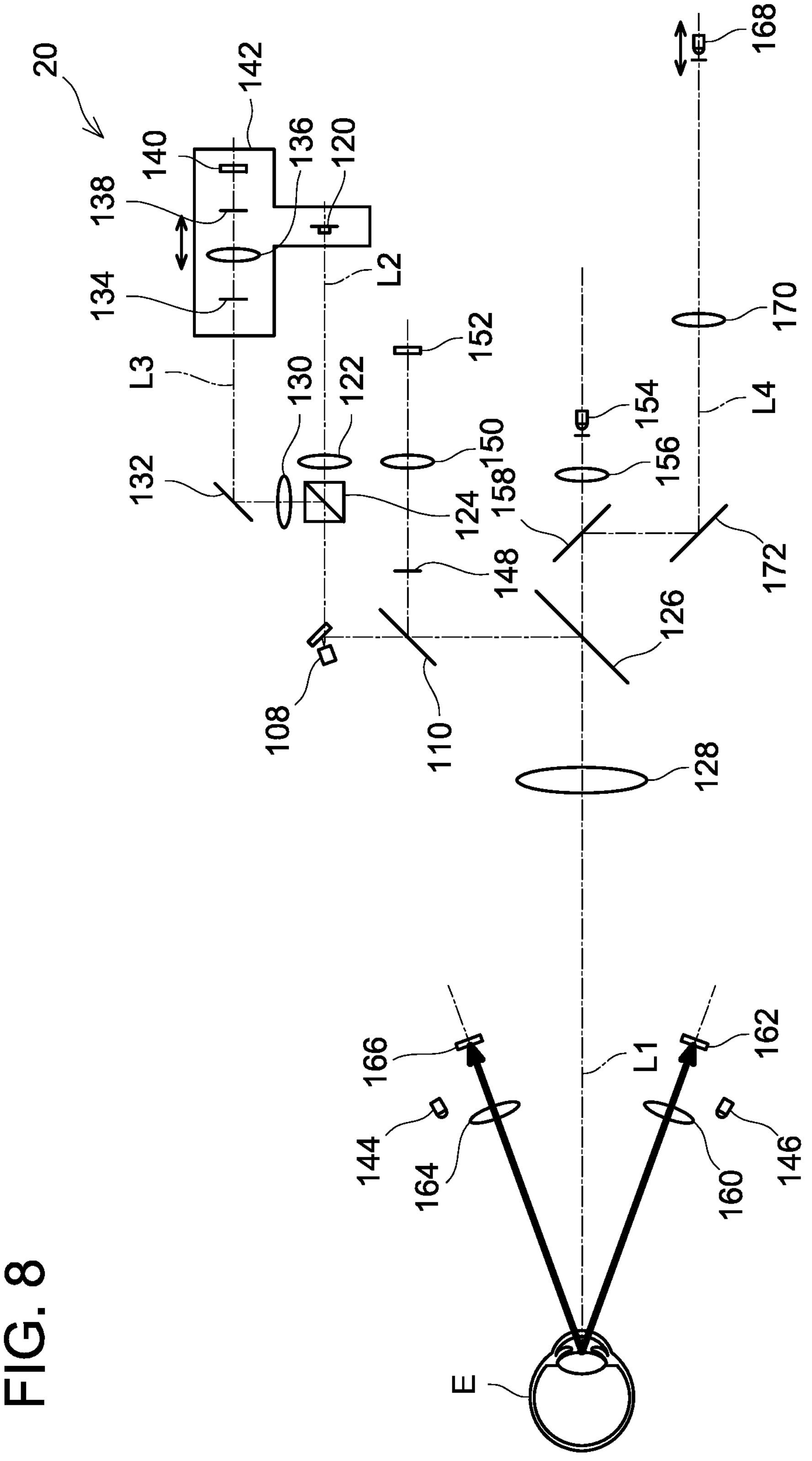
FIG. 8 is a diagram for explaining a position detection light-receiving optical system of the ophthalmic device of the first embodiment.

Next, the position detecting light-receiving optical system will be described. The position detecting light-receiving optical system is configured to detect a position of the corneal apex in a direction orthogonally intersecting the optical axis (optical path L1) (lateral direction) and further detect a position of the corneal apex in an optical axis direction (depth direction). As shown in FIG. 8, the position detecting light-receiving optical system is constituted of a lens 160, a 2D sensor 162, a lens 164, and a 2D sensor 166. The lens 160 and the 2D sensor 162 are arranged frontward of the subject eye E at positions diagonally offset toward one side. The lens 164 and the 2D sensor 166 are also arranged frontward of the subject eye E at positions diagonally offset toward another side. The lens 164 and the 2D sensor 166 are arranged at positions symmetric to the lens 160 and the 2D sensor 162 relative to the optical axis (optical path L1). The light reflected at a position slightly offset from the corneal apex of the subject eye E is reflected in an oblique direction and penetrates the lens 160, and a virtual image of the light-emitting surface of the LED 154 is projected on the 2D sensor 162. Similarly, the light reflected at a position slightly offset from the corneal apex of the subject eye E penetrates through the lens 164, and a virtual image of the light-emitting surface of the LED 154 is projected on the 2D sensor 166. In the ophthalmic device 10 of the present embodiment, the position of the corneal apex in the direction orthogonally intersecting the optical axis (optical path L1) (lateral direction) and the position of the corneal apex in the optical axis direction (depth direction) are detected based on the virtual images of the light-emitting surface of the LED 154 detected by the 2D sensors 162, 166.

Figure 9:
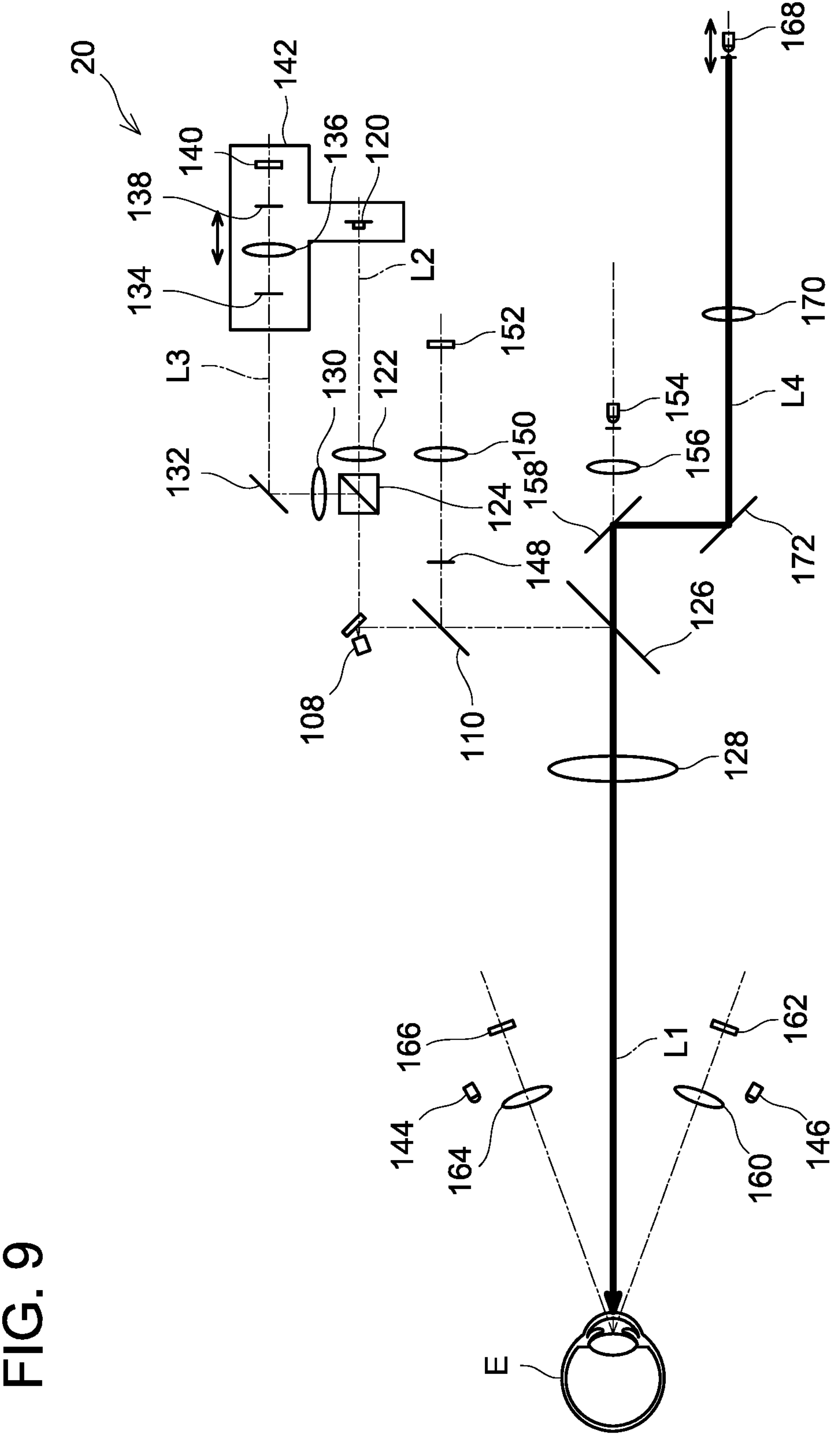
FIG. 9 is a diagram for explaining a gaze fixing optical system of the ophthalmic device of the first embodiment.

Next, the gaze fixing optical system will be described. As shown in FIG. 9, the gaze fixing optical system is constituted of a LED 168, a lens 170, a mirror 172, the dichroic mirrors 158, 126, the object lens 128, and a dichroic mirror 116. The LED 168 outputs white light. The light from the LED 168 penetrates an image film on which a symbol for the subject to fix his/her gaze is printed, and is reflected on the mirror 172. The light reflected on the mirror 172 is reflected in the dichroic mirror 158, penetrates the dichroic mirror 126, the object lens 128, and the dichroic mirror 116 and is irradiated toward the subject eye E. The LED 168 and the image film are configured to move in the optical axis direction (direction along an optical path L4), and their positions are adjusted according to the refractive power of the subject eye E.

Next, a process of measuring the eye refractive power of the subject eye E using the ophthalmic device 10 will be described. Firstly, when an examiner inputs an instruction to start an examination to an operation unit of the ophthalmic device 10 (such as a touch panel monitor), an arithmetic device (not shown) executes alignment of the subject eye E and the ophthalmic device 10. The alignment is executed using the position detecting optical systems (FIGS. 7 and 8) which the ophthalmic device 10 comprises. Since the method of alignment is well known, the detailed description thereof will be omitted.

When the alignment of the subject eye E and the ophthalmic device 10 is completed, the arithmetic device executes refractive power measurement. The refractive power measurement is executed in the following steps. Firstly, the arithmetic device adjusts the 2D scanner 108. In doing so, the arithmetic device adjusts a scanning diameter to be scanned and an irradiation position on the subject eye E based on a preset setting value range. The setting value range will be described later in detail.

Figure 10:
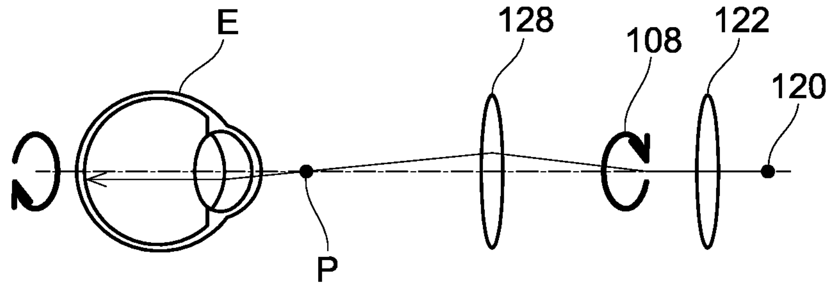
FIG. 10 schematically shows an optical path of the light-emitting optical system in the refractive power measurement optical system.

When the adjustment of the 2D scanner 108 is completed, the arithmetic device turns on the light source 120. FIG. 10 shows the optical path in which the beam outputted from the light source 120 is irradiated to the subject eye E in the light-emitting optical system. FIG. 10 shows only some of the optical members arranged on the optical path (that is, the lens 122, the 2D scanner 108, and the object lens 128) and omits depiction of other optical members. Further, in FIG. 10, depiction of a manner in which the 2D scanner 108 scans light is simplified. As shown in FIG. 10, the beam outputted from the light source 120 travels through the lens 122, the 2D scanner 108, and the object lens 128 and a spotlight-shaped light is irradiated on the fundus of the subject eye E. At this occasion, the 2D scanner 108 is driven by the driving device, by which the spot-shaped light from the light source 120 is scanned in a ring shape on the subject eye E so that the light is irradiated now in a ring shape on the fundus of the subject eye E.

Figure 11:
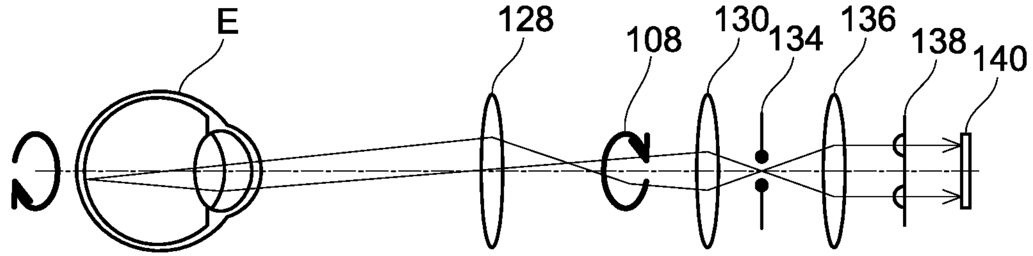
FIG. 11 schematically shows an optical path of the light-receiving optical system in the refractive power measurement optical system.

FIG. 11 shows an optical path in which the beam reflected on the fundus forms an image in the 2D sensor 140 in the light-receiving optical system. FIG. 11 shows only some of the optical members arranged on the optical path (that is, the object lens 128, the 2D scanner 108, the lens 130, the aperture 134, the lens 136, the ring lens 138, and the 2D sensor 140) and omits depiction of other optical members. The point source image projected on the fundus is reflected and scattered, and is outputted from the subject eye E, travels through the aperture 134 via the object lens 128, the 2D scanner 108, and the lens 130, and forms a ring-shaped image in the 2D sensor 140 by the lens 136 and the ring lens 138. As shown in FIG. 11, the reflected beam from the fundus is scanned inversely in the optical systems on the downstream side by the 2D scanner 108, which is shared with the light-emitting optical system, as if beam deflection did not occur to the subject eye E.

The arithmetic device reads the image outputted from the 2D sensor 140, and measures the refractive power by analyzing this image. In doing so, the fogging mechanism that is not shown may be used to measure the refractive power in a state of having excluded refraction adjustment performed by a crystalline lens of the subject eye E. Since a fogging mechanism used in known ophthalmic devices can be employed, the detailed description thereof will be omitted.

The light source 120 is arranged at a position conjugate with the fundus of the subject eye E. Due to this, the light outputted from the light source 120 can be condensed in the fundus of the subject eye E. Further, the measurement beam is scanned in the ring shape about the optical axis on the pupil of the subject eye E by the 2D scanner 108. Due to this, the measurement can be performed while avoiding opacity portions caused by cataract, for example, and deterioration in the measurement accuracy caused by speckle noise can be suppressed.

In the foregoing explanation, the ideal arrangement of the optical members for the ideal subject eye E for measuring the eye refractive power using the ophthalmic device 10 has been described. However, in the present technical field, it is known that the eye refractive power can be measured objectively with a sufficient accuracy so long as the scanning diameter of the ring-shaped beam irradiated to the fundus of the subject eye E is equal to or smaller than the diameter of the fovea of the subject eye E. Due to this, the inventors of the present application studied conditions under which the eye refractive power can be measured with high precision (that is, with a small deviation from the subjective refractive power value) in the ophthalmic device 10.

In the foregoing explanation, the light (rays) scanned by the 2D scanner 108 intersects (with each other) at the predetermined pivot position P and then enters the subject eye E, by which it reaches the fundus while being parallel to the optical axis of the ophthalmic device 10. However, in reality, the scanning diameter of the beam irradiated to the fundus may become equal to or smaller than the diameter of the fovea of the subject eye E depending on the eye axis length of the subject eye E even when the light having entered the subject eye E does not become perfectly parallel to the optical axis. That is, when the light having entered the subject eye E is not parallel to the optical axis, there are cases in which the scanning diameter becomes greater than or smaller than the diameter of the fovea depending on the eye axis length.

Hereinbelow, a condition corresponding to the eye axis length regarding the pivot position P and a beam swing angle θ of the 2D scanner 108 (an angle formed by the beam entering a subject eye lens from the pivot position P and the optical axis of the ophthalmic device 10 (which may hereinbelow be termed an incident angle θ)) for the scanning diameter to become equal to or smaller than the diameter of the fovea (that is, a maximum value of the scanning diameter becomes equal to or smaller than the diameter of the fovea) will be described.

Figure 12:
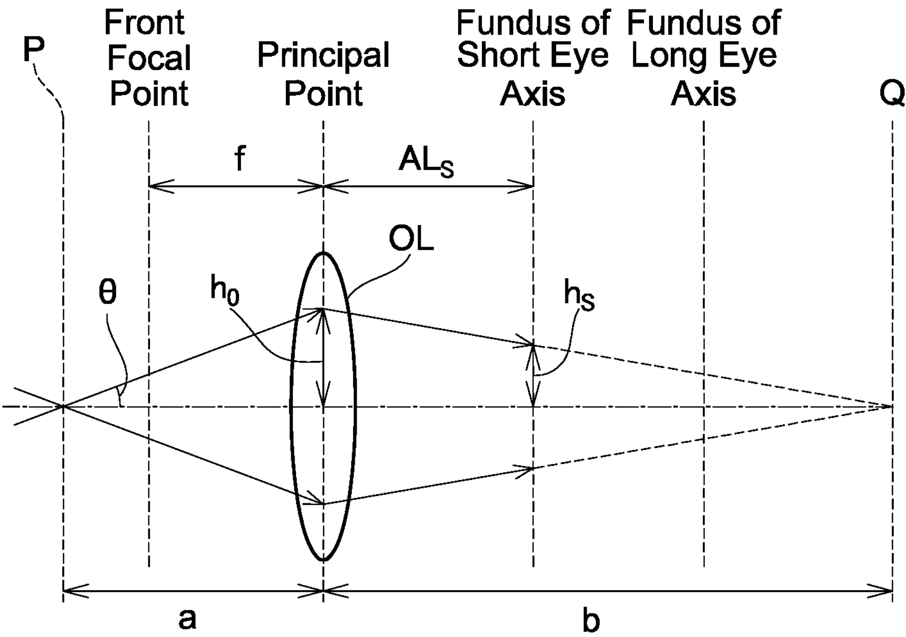
FIG. 12 is a diagram for calculating a condition equation of a pivot position and a beam swing angle for an eye with a short eye axis.

FIG. 12 shows a beam path in a case where the pivot position P is set at a position separated apart from the cornea than the focal point (front focal point) of the subject eye lens OL of the subject eye E (being a lens contemplated when the subject eye E is regarded as one lens) is from the cornea. The following formula (3) is obtained by paraxial approximation when assuming that a focal point distance of the subject eye lens OL (distance from the principal point to the front focal point) as f, a distance from the principal point of the subject eye lens OL to the pivot position P as a, and a distance from the principal point of the subject eye lens OL to a conjugate position Q of the pivot position P relative to the subject eye lens OL as b.

$$\frac{1}{f} = \frac{1}{a} + \frac{1}{b} \tag{3}$$

Since a>f stands true when the pivot position P is set as shown in FIG. 12, b becomes a positive value, and the light that penetrated the subject eye lens OL travels by refracting and being condensed at the center of the fundus (that is, gathering closer to the center of the fundus). Thus, the beam scanning diameter becomes maximum at a position just past the subject eye lens. That is, the scanning diameter of the beam irradiated to the fundus of the subject eye E becomes larger when the eye axis length of the subject eye E is shorter. As such, in setting a>f, the condition on the respective values for obtaining the maximum value of the scanning diameter that is equal to or smaller than the diameter of the fovea in the subject eye E with an eye axis length that is shorter than an average (that is, for a short-axis eye) is calculated.

Here, in assuming a height of the beam irradiated to the principal point of the subject eye lens OL (distance from the optical axis of the ophthalmic device 10) as $h_0$ and an air conversion distance from the principal point to the fundus of the short-axis eye as $AL_S$, a scanning radius (distance from the center of the fundus) $h_S$ of the beam on the fundus can be expressed by the following formula (4).

$$h_S = h_0 \frac{b - AL_s}{b} \tag{4}$$

Further, the swing angle θ of the beam can be expressed by the following formula (5).

$$h_0 = a \tan \theta \tag{5}$$

As described above, in order to measure the eye refractive power with high precision using the ophthalmic device 10, the scanning diameter needs to be equal to or smaller than the diameter of the fovea. As such, the following formula (6) needs to stand true when the diameter of the fovea is assumed as d.

$$d \geq 2h_S \tag{6}$$

From the formulas (3) to (6), the condition on the distance a from the principal point of the subject eye lens OL to the pivot position P and the swing angle θ of the beam can be expressed as in the following formula (7).

$$d \geq 2a\left\{1 - AL_s\left(\frac{1}{f} - \frac{1}{a}\right)\right\}\tan\theta \tag{7}$$

Figure 13:
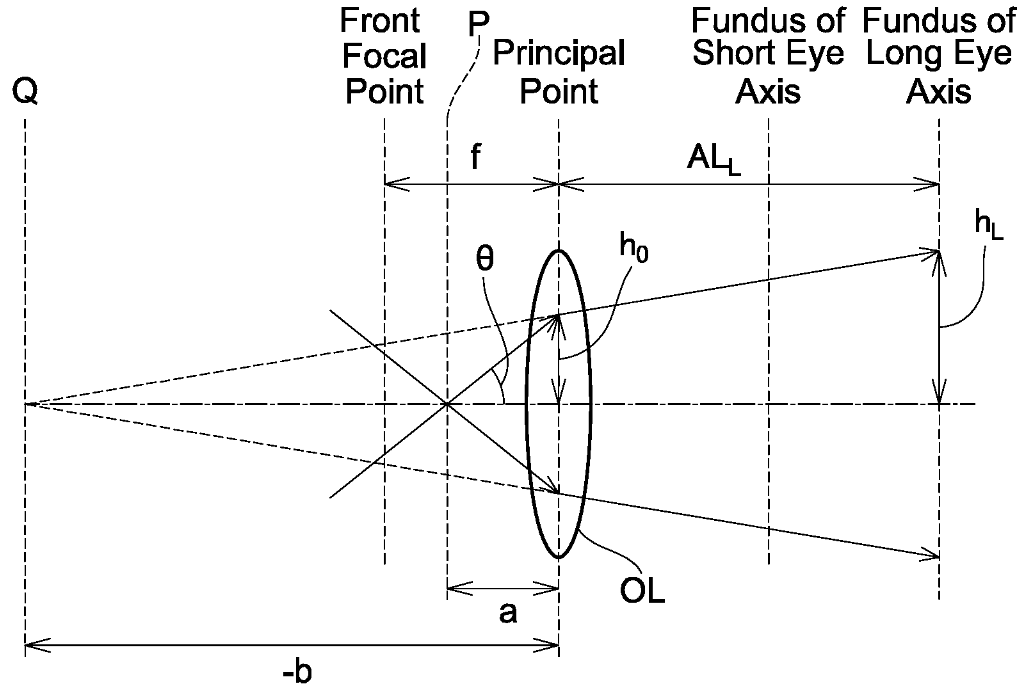
FIG. 13 is a diagram for calculating a condition equation of a pivot position and a beam swing angle for an eye with a long eye axis.

FIG. 13 shows a beam path in a case where the pivot position P is set at a position closer to the cornea than the focal point (front focal point) of the subject eye lens OL of the subject eye E is to the cornea. Since a<f stands true when the pivot position P is set as shown in FIG. 13, b becomes a negative value, and the light that penetrated the subject eye lens OL travels by refracting and being dispersed around the fundus (that is, separating away from the center of the fundus). Thus, the beam scanning diameter becomes larger at positions farther away from the subject eye lens OL. That is, the scanning diameter of the beam irradiated to the fundus of the subject eye E becomes larger when the eye axis length of the subject eye E is longer. As such, in setting a<f, the condition on the respective values for obtaining the maximum value of the scanning diameter that is equal to or smaller than the diameter of the fovea in the subject eye E with an eye axis length that is longer than the average (that is, for a long-axis eye) is calculated.

Similar to the formula (4), in assuming the air conversion distance from the principal point to a fundus of the long-axis eye as $AL_L$, a scanning radius $h_L$ of the beam on the fundus can be expressed by the following formula (8) from FIG. 13. As mentioned above, since b is a negative value, the following formula (8) is derived by setting the distance from the principal point of the subject eye lens OL to the conjugate position Q as "−b" in FIG. 13.

$$h_L = h_0\frac{-b + AL_L}{-b} = h_0\frac{b - AL_L}{b} \tag{8}$$

Thus, from the formulas (3), (5), (6), (8), the condition on the distance a from the principal point of the subject eye lens OL to the pivot position P and the swing angle θ of the beam can be expressed as in the following formula (9).

$$d \geq 2a\left\{1 - AL_L\left(\frac{1}{f} - \frac{1}{a}\right)\right\}\tan\theta \tag{9}$$

Here, the values of the diameter d of the fovea and the focal point distance f of the subject eye lens have smaller subject variations than the air conversion distances $AL_S$, $AL_L$ from the principal point to the fundus of the subject eye E. That is, in the formulas (7) and (9) as above, the diameter d and the focal point distance f can be set as fixed values. Specifically, the diameter d may be set to about 1.5 mm, which is an average fovea diameter known in the technical field. Further, the focal point distance f may be set to 1000/58.6=17.1 (mm), based on the total refractive power of the Gullstrand's schematic eye being 58.64 D.

On the other hand, for the air conversion distance $AL_S$ in the formula (7) as above, a lower limit of the short eye axis length (that is, the shortest eye axis length that should be considered) is calculated. Specifically, it can be set to 1/(1/17+15/1000)=13.6 (mm) based on +15 D being an upper limit of a refractometer measurement range specified by the international standard ISO10342: 2010 by the ISO and the focal point distance f as above. Further, for the air conversion distance $AL_L$ in the formula (9) as above, an upper limit of the long eye axis length (that is, the longest eye axis length that should be considered) is calculated. Specifically, it can be set to 1/(1/17−15/1000)=22.9 (mm) based on −15 D being a lower limit of the refractometer measurement range specified by the international standard ISO10342: 2010 and the focal point distance f as above. By substituting the aforementioned values to the formulas (7) and (9), the condition equations for the distance a and the swing angle θ can be calculated. Specifically, they can be calculated as being in ranges satisfying the following formulas (10) and (11).

$$1.5 \geq 2a\left\{1 - 13.6\left(\frac{1}{17.1} - \frac{1}{a}\right)\right\}\tan\theta \tag{10}$$

$$1.5 \geq 2a\left\{1 - 22.9\left(\frac{1}{17.1} - \frac{1}{a}\right)\right\}\tan\theta \tag{11}$$

When the eye refractive power of the subject eye E is to be actually measured, the pivot position P is set as a distance a' from the corneal apex of the subject eye E. However, since the principal point of the subject eye lens OL is located within the subject eye E, the actual distance from the corneal apex of the subject eye E to the front focal point does not equal to the focal point distance 17.1 mm. Due to this, in actually calculating the condition, the condition is calculated by correcting the distance a in the above formulas (10) and (11) to a=a'−15.7+17.1=a'+1.4 (mm) based on the distance from the corneal apex of the Gullstrand's schematic eye to the front focal point being 15.7 mm.

Figure 14:
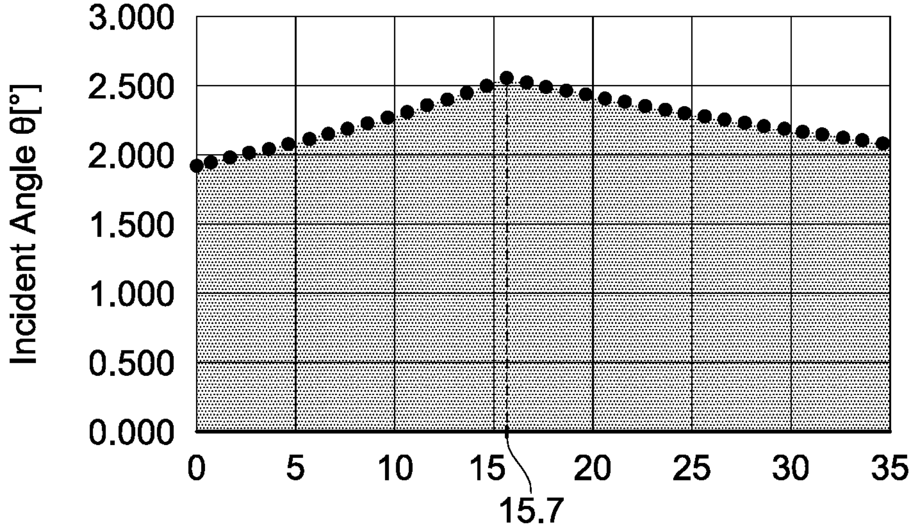
FIG. 14 is a graph showing a range in which the pivot position and the beam swing angle satisfy their condition.

FIG. 14 is a graph showing a range that satisfies the formulas (10) and (11) (hatched region). By setting the distance a' and the incident angle θ to values within the hatched region shown in FIG. 14, the scanning diameter of the beam scanned in the ring shape can be set to be equal to or smaller than the diameter of the fovea of the subject eye E regardless of the eye axis length of the subject eye E. That is, the eye refractive power can be measured with high precision. In the present embodiment, the beam (i.e., rays) deflected by the 2D scanner 108 is set to form the pivot in front of the subject eye E. Due to this, in FIG. 14, values on vertical and horizontal axes (that is, a'=0 mm, θ=0°) are not included in the condition.

Second Embodiment

Figure 15:
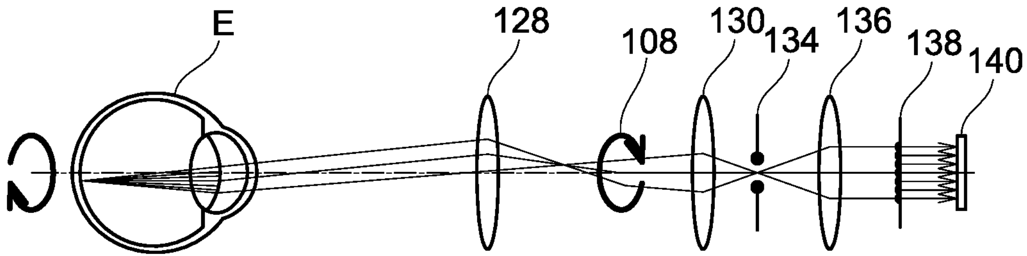
FIG. 15 is a diagram corresponding to FIG. 11 and schematically showing an optical path of a light-receiving optical system in a refractive power measurement optical system of an ophthalmic device of a second embodiment.
Figure 16:
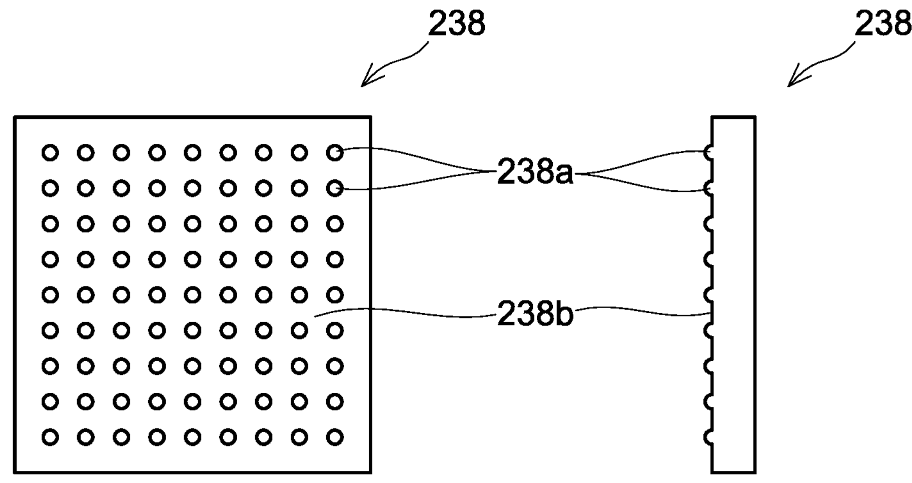
FIG. 16 is a diagram for explaining a configuration of a lens array.

In the first embodiment, the light scattered on the fundus of the subject eye E is caused to form an image in the ring shape on the light receiving surface of the 2D sensor 140 by using the ring lens 138. In a second embodiment, as shown in FIG. 15, a lens array 238 (an example of optical member) is arranged instead of the ring lens 138. As shown in FIG. 16, the lens array 238 is constituted of a plurality of lenses 238*a* arranged in a grid pattern on a flat plate and a light-blocked part 238*b* on which coating for blocking light is applied in a range excluding the lenses 238*a*. Similar to the ring lens 138 of the first embodiment, the lens array 238 is arranged at a position at which the light-blocked part 238*b* becomes conjugate with the fundus of the subject eye E. Due to this, the reflected light from the fundus is extracted from around the pupil in a dot grid pattern corresponding to the light-blocked part 238*b*. When the reflected light enters the lens array 238, a dot-patterned image corresponding to the respective lenses 238*a* is formed on the detection surface of the 2D sensor 140. In the present embodiment, the refractive power of the subject eye E is calculated based on the dot pattern formed in the 2D sensor 140. For example, a wavefront distortion in a wavefront generated by the eyeball of the subject eye E (that is, the total aberration of the eyeball) can be measured by detecting position coordinates of the respective dots formed in the 2D sensor 140.

Third Embodiment

Figure 17:
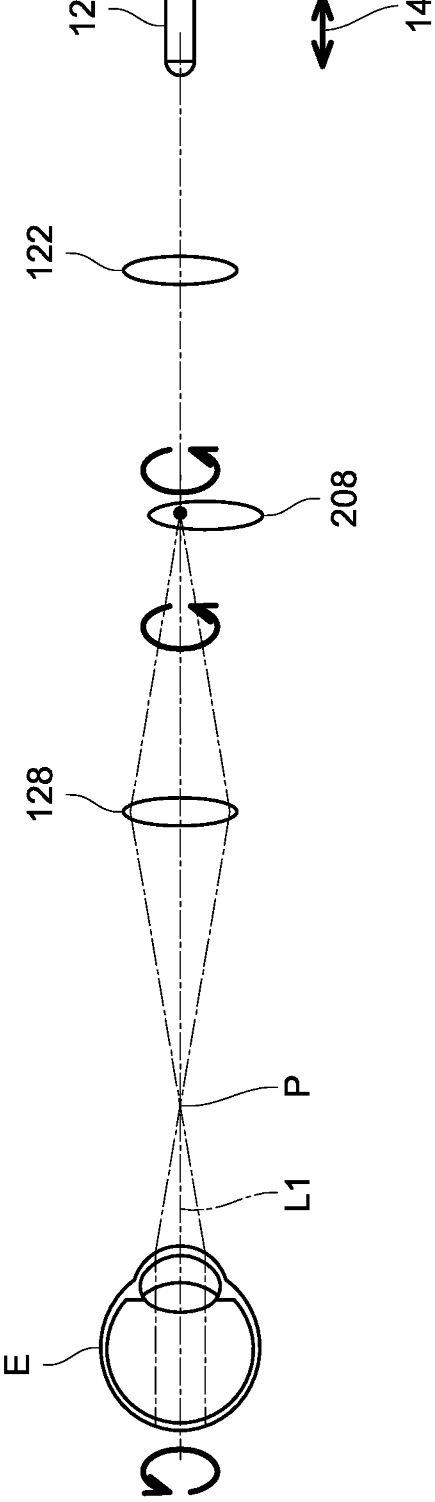
FIG. 17 is a diagram corresponding to FIG. 5 and schematically showing an optical path of light in a light-emitting optical system in a refractive power measurement optical system of an ophthalmic device of a third embodiment.

In an ophthalmic device of a third embodiment, as shown in FIG. 17, a relay lens 208 is arranged instead of the 2D scanner 108 of the first embodiment. Similar to the 2D scanner 108 of the first embodiment, the relay lens 208 is arranged at a position conjugate with the pivot position P. The relay lens 208 is configured to be driven in a ring shape about an optical axis of the ophthalmic device on a plane orthogonally intersecting the optical axis of the ophthalmic device by a driving device that is not shown (such as a hollow motor and voice coil motor (VCM)). In the present embodiment, the relay lens 208 is eccentrically offset in a ring shape from the optical axis of the ophthalmic device, and the beam entering the relay lens 208 is thereby deflected and can be scanned in the ring shape on the fundus of the subject eye E. In the present embodiment, the beam can be scanned in the ring shape at low cost by combining the relay lens 208 and the driving device such as the VCM.

Fourth Embodiment

Figure 18:
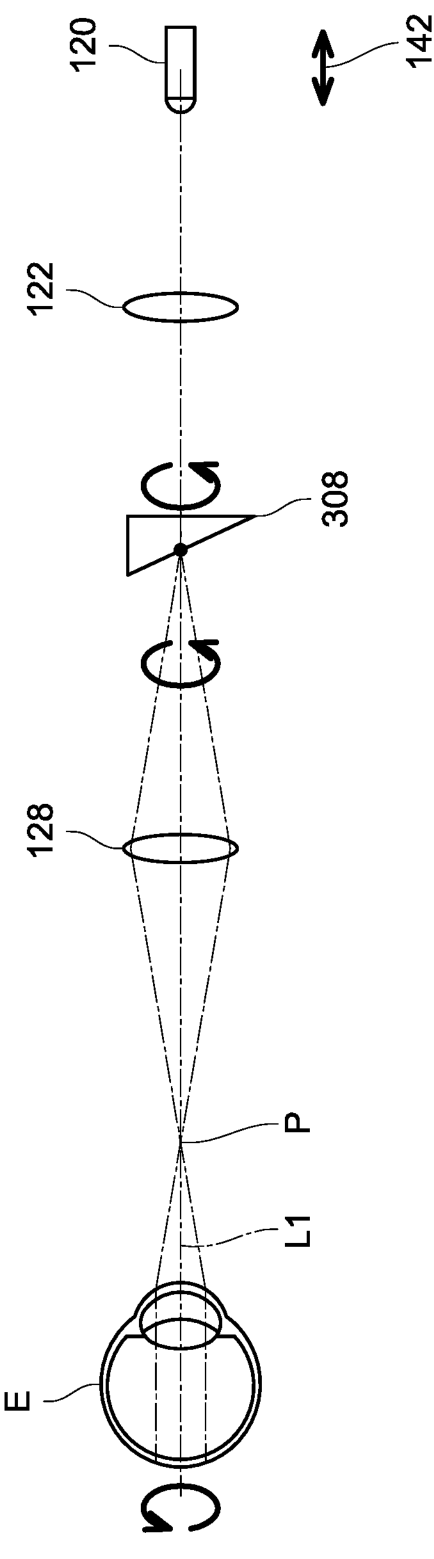
FIG. 18 is a diagram corresponding to FIG. 5 and schematically showing an optical path of light in a light-emitting optical system in a refractive power measurement optical system of an ophthalmic device of a fourth embodiment.

In an ophthalmic device of a fourth embodiment, as shown in FIG. 18, a wedge-shaped prism 308 is arranged instead of the 2D scanner 108 of the first embodiment. Similar to the 2D scanner 108 of the first embodiment, the prism 308 is arranged at a position conjugate with the pivot position P. The prism 308 is driven about an optical axis by a driving device that is not shown (such as a hollow motor). In the present embodiment, the prism 308 rotates about the optical axis, and the beam entering the prism 308 can be deflected and scanned in the ring shape on the fundus of the subject eye E. In the present embodiment as well, the beam can be scanned in the ring shape at low cost by combining the prism 308 and the hollow motor.

Fifth Embodiment

Figure 19:
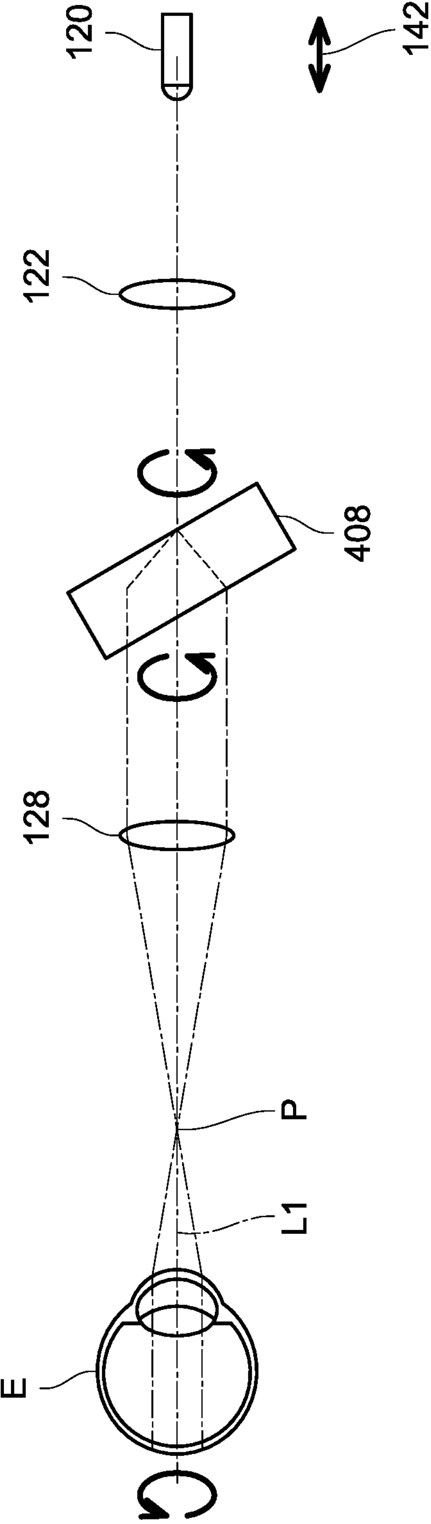
FIG. 19 is a diagram corresponding to FIG. 5 and schematically showing an optical path of light in a light-emitting optical system in a refractive power measurement optical system of an ophthalmic device of a fifth embodiment.

In an ophthalmic device of a fifth embodiment, as shown in FIG. 19, a planar parallel plate 408 is arranged instead of the 2D scanner 108 of the first embodiment. In the present embodiment, a thickness and a tilt angle of the planar parallel plate 408 are adjusted so as to form a pivot at a position at the focal point distance of the object lens 128. The planar parallel plate 408 is driven about an optical axis by a driving device that is not shown (such as a hollow motor). In the present embodiment, the planar parallel plate 408 rotates about the optical axis, by which the beam entering the planar parallel plate 408 is outputted from around the optical axis in the same traveling direction as the entering beam (i.e., in the optical axis direction). That is, the planar parallel plate 408 rotates, by which the beam parallel to the optical axis and scanned in the ring shape is outputted from the planar parallel plate 408. As such, in this embodiment as well, the beam outputted from the light source 120 can be scanned in the ring shape on the fundus of the subject eye E.

While specific examples of the present disclosure have been described above in detail, these examples are merely illustrative and place no limitation on the scope of the patent claims. The technology described in the patent claims also encompasses various changes and modifications to the specific examples described above. The technical elements explained in the present description or drawings provide technical utility either independently or through various combinations. The present disclosure is not limited to the combinations described at the time the claims are filed. Further, the purpose of the examples illustrated by the present description or drawings is to satisfy multiple objectives simultaneously, and satisfying any one of those objectives gives technical utility to the present disclosure.

What is claimed is:

1. An ophthalmic device comprising:

a measurement optical system which includes a light-emitting optical system including a light source configured to emit light beam in a spot shape onto a fundus of a subject eye and a light-receiving optical system including a light receiving element configured to receive reflected light from the fundus of the subject eye;

an arithmetic device configured to calculate an eye refractive power of the subject eye based on an output of the light receiving element;

a beam deflecting member arranged in an optical path of the measurement optical system and configured to deflect the beam emitted from the light source; and a driving device configured to drive the beam deflecting member so that the beam emitted from the light source is scanned in a ring shape onto the subject eye;

wherein the beam deflecting member is disposed so that traveling directions of the beam emitted from the light source intersect with each other between the subject eye and the beam deflecting member when the beam deflecting member is driven by the driving device.

2. The ophthalmic device according to claim 1, wherein the beam deflecting member is arranged at a position conjugate with an intersecting position where the traveling directions of the beam intersect with each other.

3. The ophthalmic device according to claim 1, wherein the light-receiving optical system further includes an optical member arranged at a position conjugate with the fundus of the subject eye and configured to condense the reflected light in a ring shape on the light receiving element.

4. The ophthalmic device according to claim 1, wherein the light receiving optical system further includes an optical member having a plurality of lenses arranged in a grid pattern at a position conjugate with the fundus of the subject eye, the lenses being configured to condense the reflected light in a shape of dots constituting a grid pattern on the light-receiving element.

5. The ophthalmic device according to claim 1, wherein the driving device is configured to drive the beam deflecting member so that the traveling directions of the beam entering the subject eye are substantially parallel inside the subject eye.

6. The ophthalmic device according to claim 1, wherein if a>f, a position of the beam deflecting member or a swing angle of the beam is set so as to satisfy the following formula:

$$1.5 \geq 2(a' + 1.4)\left\{1 - 13.6\left(\frac{1}{17.1} - \frac{1}{a' + 1.4}\right)\right\}\tan\theta;$$

if a<f, the position of the beam deflecting member or the swing angle of the beam is set so as to satisfy the following formula:

$$1.5 \geq 2(a' + 1.4)\left\{1 - 22.9\left(\frac{1}{17.1} - \frac{1}{a' + 1.4}\right)\right\}\tan\theta$$

where a is a distance from a principal point of a subject eye lens to an intersecting position where the traveling directions of the beam intersect with each other, f is a focal length of the subject eye lens and is 17.1 mm, a diameter of a fovea of the subject eye is 1.5 mm, a' is a distance from a corneal apex of the subject eye to the intersecting position, and θ is an angle formed by the beam entering the subject eye lens from the intersecting position and an optical axis of the ophthalmic device.

* * * * *